United States Patent [19]
Crivello et al.

[11] Patent Number: 5,169,962
[45] Date of Patent: Dec. 8, 1992

[54] PREPARATION OF EPOXYSILICON COMPOUNDS USING RHODIUM CATALYSTS

[75] Inventors: James V. Crivello, Clifton Park; Ming-Xin Fan, Troy, both of N.Y.

[73] Assignee: General Electric Company, Waterford, N.Y.

[21] Appl. No.: 583,524

[22] Filed: Sep. 17, 1990

[51] Int. Cl.$^5$ ............................................. C07F 7/02
[52] U.S. Cl. ................................................. 549/215
[58] Field of Search ....................................... 549/215

[56] References Cited

U.S. PATENT DOCUMENTS

| | | | |
|---|---|---|---|
| 3,928,629 | 12/1975 | Chandra et al. | 427/387 |
| 4,279,717 | 7/1981 | Eckberg et al. | 204/159.13 |
| 4,804,768 | 2/1989 | Quirk et al. | 549/215 |
| 4,952,657 | 8/1990 | Riding et al. | 549/215 |
| 4,961,963 | 10/1990 | Peters | 528/32 |
| 5,037,861 | 8/1991 | Crivello et al. | 549/215 |

OTHER PUBLICATIONS

J. F. Harrod and A. J. Chalk, "Organic Syntheses via Metal Carbonyls", vol. 2, I. Wender and P. Pino, editors, John Wiley, N.Y. 1977.

J. L. Speier, Adv. in Organomet. Chem., vol. 17, pp. 432-434.

Primary Examiner—Melvyn I. Marquis
Assistant Examiner—Karen A. Hellender

[57] ABSTRACT

A method for making an epoxyfunctional organosilicon compound is provided, comprising the step of reacting at a temperature of from about 25° to about 100° C. a mixture comprising (A) an ethylenically unsaturated epoxide; (B) an organohydrogenpolysiloxane or organohydrogensilane; and (C) a rhodium complex catalyst selected from the group consisting of:

(i) $RhX_3(SR_2)_3$;
(ii) $RhX_3 \cdot xH_2O$;
(iii) $[RhX(norbornadiene)]_2$;
(iv) $RhX(CO)(R_3P)_3$;
(v) $RhX(R_3P)_3$; and
(vi) $[RhCl(cyclooctadiene)]_2$;

wherein X is a halogen atom, x is a number equal to 3 or 4, and R is an alkyl radical having from 1 to 8 inclusive carbon atoms, aryl, aralkyl, or alkaryl radical or the $R_3^1SiQ$— group in which Q represents a divalent aliphatic hydrocarbon radical having from 1 to 6 inclusive carbon atoms and $R^1$ represents an alkyl radical having from 1 to 8 inclusive carbon atoms, aryl, aralkyl, or alkaryl radical or a $(CH_3)_3Si$— radical.

14 Claims, No Drawings

PREPARATION OF EPOXYSILICON COMPOUNDS USING RHODIUM CATALYSTS

BACKGROUND OF THE INVENTION

The present invention relates to hydrosilation catalysts which promote the addition of unsaturated epoxides to SiH-containing siloxanes and silanes. More particularly, the present invention relates to certain rhodium-based hydrosilation catalysts which promote the addition of unsaturated epoxides to SiH-containing siloxanes and silanes without promoting ring opening polymerization of the epoxide.

Epoxy-silicone monomers, oligomers, and polymers are usually prepared by a hydrosilation addition reaction between an olefin epoxide and a SiH-containing siloxane or silane in the presence of a platinum or platinum-based hydrosilation catalyst. Such reactions are described, for example, in copending, commonly assigned application Ser. No. 07/332,646, filed Apr. 3, 1989, and in U.S. Pat. No. 4,279,717 (Eckberg).

However, it has been found that in addition to catalyzing the olefin and SiH addition reaction, platinum catalysts also catalyze the ring-opening polymerization of the epoxide in the presence of SiH. Copending, commonly assigned application Ser. No. 07/473,802 (Riding et al.), filed Feb. 2, 1990, discloses the use of platinum or platinum-based catalysts to promote the ring opening of epoxides. The ring-opening polymerization of the epoxide during production of the epoxysilicone is undesirable because such polymerization causes the reaction mixture to gel completely, resulting in loss of the entire batch and in loss of considerable time in cleanup of the insoluble gelled resin.

In addition, partial ring opening polymerization can result in irreproducible batch-to-batch variations in the viscosity. Good viscosity control is essential in critical coating applications such as those involved in paper release coatings.

It has been observed that epoxy-silicone monomers stored in the presence of a platinum catalyst have a tendency to gel on standing due to slow ring opening polymerization at room temperature.

Thus far, epoxysilicone fluids have been successfully produced by careful control of batch temperature and olefin-epoxide feed rate during the synthesis and by sue of low levels of mercaptans, e.g., dodecyl mercaptan or 2-mercaptobenzothiazole, to de-activate platinum catalyst after the hydrosilation reaction. However, there remains sufficient possibility of the ring opening polymerization occurring that each batch could result in gelling of a large reactor.

The present invention is based on the discovery that certain rhodium-based catalysts are effective for promoting the addition of olefin-epoxides to SiH-containing siloxanes and silanes without promoting the ring opening polymerization of the epoxide starting material or final product.

The use of rhodium-based catalysts for promoting the hydrosilation of olefinic substrates which are not epoxy-functionalized is known in the art. Reference is made to J. F. Harrod and A. J. Chalk, in "Organic Syntheses via Metal Carbonyls", Vol. 2, I. Wender and P. Pino, editors, John Wiley, N.Y. 1977, pages 685–687; and J. L. Speier, Adv. in Organomet. Chem., Vol. 17, 407 (1979).

Hydrosilation reactions between olefinic epoxides and organohydrogenpolysiloxanes catalyzed with platinum metal complexes containing rhodium, ruthenium, palladium, osmium, and iridium are also known in the art. Reference is made, for example, to copending, commonly assigned application Ser. Nos. 07/332,646, filed Apr. 3, 1989, and Ser. No. 07/473,802, filed Feb. 2, 1990, and U.S. Pat. No. 4,279,717 (Eckberg).

It is therefore an object of the present invention to provide a method for preparing epoxysilicon compounds by means of a hydrosilation reaction between an unsaturated epoxide and an SiH-containing silicon compound in the presence of a hydrosilation catalyst which promotes the hydrosilation reaction without promoting the ring opening polymerization of the epoxide ring in either the unsaturated epoxide starting material or the epoxysilicon product.

It is another object of the present invention to provide a hydrosilation catalyst for the addition reaction between an unsaturated epoxide and a SiH-containing silicon compound to form an epoxysilicon compound, wherein the catalyst effectively promotes the hydrosilation reaction without promoting the ring opening polymerization of the epoxide ring in either the unsaturated epoxide starting material or the epoxysilicon product.

These objects and others are achieved in the present invention.

SUMMARY OF THE INVENTION

The present invention provides a method for making an epoxyfunctional organosilicon compound, comprising the step of reacting at a temperature of from about 25° to about 100° C. a mixture comprising:

(A) 1 part by weight of an ethylenically unsaturated epoxide;

(B) from about 0.5 to about 400 parts by weight based on (A) of an organohydrogenpolysiloxane or organohydrogensilane; and (C) from about 1 to about 5000 parts per million based on (A) of a rhodium complex catalyst selected from the group consisting of:

(i) $RhX_3(SR_2)_3$;

(ii) $RhX_3 \cdot xH_2O$;

(iii) $[RhX(norbornadiene)]_2$;

(iv) $RhX(CO)(R_3P)_3$;

(v) $RhX(R_3P)_3$; and (vi) $[RhCl(cyclooctadiene)]_2$;

wherein X is a halogen atom, x is a number equal to 3 or 4, and R is an alkyl radical having from 1 to 8 inclusive carbon atoms, aryl, aralkyl, or alkaryl radical or the $R_3^1SiQ$- group in which Q represents a divalent aliphatic hydrocarbon radical having from 1 to 6 inclusive carbon atoms and $R^1$ represents an alkyl radical having from 1 to 8 inclusive carbon atoms, aryl, aralkyl, or alkaryl radical or a $(CH_3)_3Si$- radical.

The invention is further directed to the curable composition comprising components (A)–(C) used in the method described above.

By suppressing the undesirable ring opening polymerization of the epoxide starting materials and products while promoting the SiH-olefin hydrosilation reaction, the catalyst used in the method of the present invention allows the synthesis of epoxy-containing monomers, oligomers, and polymers without the complication of either premature gelation or variations in viscosity and produces storage stable resins and monomers.

DETAILED DESCRIPTION OF THE INVENTION

Component (A) used in the method and composition of this invention is an ethylenically, i.e., either vinyl- or allyl-functional, epoxide. The vinyl- or allyl-functional epoxides contemplated are any of a number of aliphatic (glycidyl) or cycloaliphatic epoxy compounds having olefinic moities which will readily undergo addition reaction to =SiH-functional groups. Commercially available examples of such compounds include allyl glycidyl ether, methallyl glycidyl ether, 1-methyl-4-isopropenyl cyclohexeneoxide; 2,6-dimethyl-2,3-epoxy-7-octene; 1,4-dimethyl-4-vinylcyclohexeneoxide; 4-vinylcyclohexeneoxide; vinylnorborenemonoxide, and dicyclopentadienemonoxide. The preferred epoxide is 4-vinylcyclohexeneoxide.

Component (B) is an organohydrogensiloxane or organohydrogensilane. Suitable silicon hydride-containing starting materials include any silicon compound derived from at least two organosiloxane units and having terminal and/or pendant Si-H groups. The Si-H functional silicon compound is capable of reacting with the olefinic moieties of the above-mentioned epoxides via addition reaction.

Component (B) can be either a linear hydride polysiloxane or silane or a cyclic hydride polysiloxane or silane.

Examples of suitable linear Si-H functional silicon compounds include 1,1,3,3-tetraalkyldisiloxane, dialkyl-hydrogensiloxy-endstopped polydialkylsiloxane, polydialkylalkylhydrogen-siloxane copolymer, and trialkylsiloxy-endstopped polydialkyl-alkylhydrogensiloxane copolymer comprising at least two alkylhydrogen siloxy groups. Other examples of Si-H containing silicon compounds include 1,1,3,3-tetramethyldisiloxane, 2,4,6,8-tetramethylcyclotetrasiloxane, methyldimethoxysilane, triethylsilane, and methyldiethoxysilane. The preferred linear Si-H functional silicon compound as a starting material for making the epoxy functional silicone used in the present invention is 1,1,3,3-tetramethyldisiloxane.

Preferably, the cyclic hydride polysiloxane is hydride cyclotetrasiloxane.

Preferably, component (B) is the aforementioned 1,1,3,3-tetramethyldisiloxane.

Component (B) is used in the method and composition of this invention in an amount ranging from about 0.5 to about 400, preferably from about 0.5 to about 100, and most preferably from about 0.75 to about 5.0, parts by weight based on component (A).

Component (C) is a rhodium-based catalyst selected from the group consisting of:

(i) $RhX_3(SR_2)_3$;
(ii) $RhX_3 \cdot xH_2O$;
(iii) $[RhX(norbornadiene)]_2$;
(iv) $RhX(CO)(R_3P)_3$;
(v) $RhX(R_3P)_3$; and
(vi) $[RhCl(cyclooctadiene)]_2$;

In the general formulae (i)–(vi), each X may represent a halogen atom, preferably chlorine. The letter x in formula (ii) is a number equal to 3 or 4. The R substituents in formulae (i), (iv), and (v) may be the same or different in any given complex and may be an alkyl radical having from 1 to 8 inclusive carbon atoms, aryl, aralkyl, or alkaryl radicals, for example, methyl, ethyl, n-butyl, hexyl, phenyl, tolyl, and benzyl. The R substituents may also represent $R_3^1SiQ$- groups in which Q represents a divalent aliphatic hydrocarbon radical having from 1 to 6 inclusive carbon atoms, e.g., —$CH_2$—, —$CH_2$—$CH_2$—, and —$CH_2CHCH_3$—$CH_2$—, and each $R^1$ represents an alkyl, aryl, aralkyl, or alkaryl radical as defined and exemplified for R, or one $R^1$ substituent may represent a trimethylsilyl radical.

Sulphur-containing complexes having the general formula (i) and methods for preparing them are disclosed, for example, in U.S. Pat. No. 3,928,629 (Chandra et. al), which is hereby incorporated by reference herein. As discussed in the Chandra et al. patent, complexes of the formula (i) in which the R substituents do not contain silicon can be prepared, for example, according to the disclosure in Jour. Chem. Soc., (A), (1971), 899, which is also hereby incorporated by reference herein. Complexes having the general formula (i) which contain silicon may be prepared by reacting together a rhodium halide $RhX_3$ and a silicon-containing sulphide $R_2S$, preferably in the presence of a polar solvent.

Complexes of the general formula (ii) are commercially available and may be prepared by dissolving hydrated $Rh_2O_3$ in aqueous HX (wherein "X" is as previously defined herein) acids and then evaporating the resultant solutions. $RhX_3 \cdot xH_2$) is normally considered to be about 40% Rh, with x being equal to 3 or 4.

Complexes of the general formula (iii) may be prepared by reacting $RhX_3 \cdot xH_2O$ with excess norbornadiene in ethanol, wherein X and x are as defined above.

Complexes of the general formula (iv) may be prepared as described in J. Chem. Soc., (1965), 1900, which is incorporated by reference herein.

Complexes of the general formula (v) may be prepared by reacting $RhX_3 \cdot xH_2$) with excess triphenylphosphine in hot ethanol, wherein X and x are as defined above.

Complexes of the general formula (vi) may be prepared by reacting $RhX_3xH_2O$ with excess 1,4-cyclooctadiene in ethanol, similar to the preparation of complexes (iii), wherein X and x are as defined above.

The rhodium-based catalyst is used in an amount sufficient to give the rate of cure desired in the composition. In general, the catalyst is best used in an amount of from about 1 to about 5000 parts per million, preferably from about 1 to about 500, and most preferably from about 10 to about 50, parts by weight based on component (A).

The preferred rhodium-based catalyst for use in the present invention is $RhX(R_3P)_3$ and most preferably $RhCl(Ph_3P)_3$, wherein "Ph" represents a phenyl group.

The epoxysilicon product formed from the composition and method of this invention is prepared by reacting components (A), (B), and (C) at a temperature in the range of from about 25° C. to about 125° C.

The addition and dispersion of this composition is facilitated if it is added as a solution or dispersion in an inert liquid carrier, e.g., hexane or toluene. The amount of volatile liquid carrier incorporated into the composition should not exceed about 3% by weight based on the total weight of the composition if the advantages of using a substantially solvent-free composition are to be retained.

If component (B) is a linear SiH-containing silicon compound, the epoxysilicon compounds formed from the composition and method described above can be represented by the general formula:

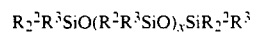

wherein each $R^2$ individually is an alkyl group having from 1 to 8 carbon atoms, each $R^3$ individually is $R^2$ or a monovalent epoxyfunctional organic radical having from 2 to 20 carbon atoms with the proviso that at least 2 $R^3$ groups are monovalent epoxyfunctional organic radicals and x has a value of 0 to 400.

If component (B) is a hydride cyclotetrasiloxane, the epoxysilicon compound formed from the composition and method of the present invention can be represented by the general formula $D_4'$, which represents an epoxy cyclotetrasiloxane.

The epoxyfunctional silicon compounds produced in the method of this invention can be combined with a miscible bis-aryl iodonium, sulfonium or other onium-type cationic salt photoinitiator, after which an ultraviolet light cure reaction can be initiated in order to form a final product such as a solventless silicone release coating.

In order that persons skilled in the art may better understand the practice of the present invention, the following examples are provided by way of illustration, and not by way of limitation.

EXPERIMENTAL

In the examples below:

"M" represents a monovalent $(CH_3)_3SiO_{1/2}$ unit;
"$M^H$" represents a monovalent $(CH_3)_2SiO_{1/2}$ unit;
"D" represents a divalent $(CH_3)_2SiO_{2/2}$ unit; and
"$D^H$" represents a divalent $(CH_3)HSiO_{2/2}$ unit.
"Q" represents a tetravalent $SiO_{4/2}$ unit.

EXAMPLE 1

Example 1 illustrates the preparation of poly[methyl 2-ethyl(3-epoxycyclohexyl)siloxane]. 20 mL of toluene, 3.0 grams of poly(methylhydrogensiloxane), 6.7 grams of VCHO and 5 mg of $RhCl(Ph_3P)_3$ were combined in a 100 mL round bottom flask. The reaction flask was fitted with a magnetic stirrer and a reflux condenser. The mixture was heated at 100° C. for three days. After cooling, the product was isolated by removing the solvent on a rotary evaporator and removing the last traces of solvent in a vacuum oven.

EXAMPLE 2

Example 2 illustrates the preparation of a cyclic tetrafunctional epoxysilicone monomer. Using the same apparatus as used in Example 1, a mixture containing 13.1 grams of VCHO, 6.0 grams of 2,4,6,8-tetramethylcyclotetrasiloxane, 30 mL of toluene, and 5 mg of $RhCl(Ph_3P)_3$ was heated at 100° C., under constant stirring, for four days. After this time, the product was isolated in quantitative yield by removal of the solvent with a rotary evaporator.

EXAMPLE 3

Example 3 illustrates the effect of the hydrosilation catalyst on ring opening polymerization.

1.0 gram of cyclohexene oxide was added to 1.0 gram of 1,1,3,3-tetramethyldisiloxane and 5 mg of $RhCl(Ph_3P)_3$. No reaction was observed. When this procedure was repeated using the same amount of a platinum-containing Ashby catalyst (i.e., a platinum complex of divinyltetramethyldisiloxane, as described in U.S. Pat. No. 4,288,345 to Ashby et al.) in place of the rhodium-containing catalyst, rapid, exothermic polymerization was noted. Similar observations were made using the Lamoreaux catalyst (i.e., $H_2PtCl_6$ in octyl alcohol, as described in U.S. Pat. No. 3,220,972); speier catalyst (i.e., chloroplatinic acid); and Karstedt catalyst (platinum-siloxane complex containing less than 0.1 gram atom of halogen per gram atom of platinum).

EXAMPLE 4

10.0 grams of 4-vinylcyclohexeneoxide and 5.6 grams of 1,1,3,3-tetramethyldisiloxane were combined and placed into a 100 mL round bottom flask equipped with a magnetic stirrer and reflux condenser. To the mixture was added 5 mg of $RhCl(Ph_3)_3$ and 30 mL toluene. The resulting mixture was heated at 100° C. for two days while stirring. The final product was isolated in quantitative yield by removing the solvent on a rotary evaporator. Size exclusion chromatography revealed the absence of any high molecular weight (polymers from ring opening polymerization) in the product.

EXAMPLE 5

VCHO (25.4 grams, 0.205 mole) was weighed into a 100 cc flask equipped with a magnetic stirrer. To this was added solid $RhCl(Ph_3P)_3$ (0.01 grams), which rapidly dissolved in the VCHO. This solution was brought to 82° C., at which point 13.7 grams of symtetramethyldisiloxane ($M^H M^H$) were added dropwise. After a brief induction period during which about one-half of the $M^H M^H$ was added, a sudden exotherm occurred which raised the batch temperature to 130° C. Addition was halted until the batch temperature was reduced to 90° C. Resumption of $M^H M^H$ feed brought on a second exotherm of more than 120° C. The $M^H M^H$ addition was again stopped and the batch temperature reduced to 90° C. The remainder of the $M^H M^H$ was then added. The complete reaction mixture was maintained at 90° C. overnight, after which time no SiH was detected by means of FTIR. Unreacted VCHO was removed by maintaining the batch at 145° C. under a strong nitrogen sweep for 2 hours. 36 grams of a mobile (50 centistoke viscosity), clear liquid product, $N_D^{25} = 1.4736$, were ultimately obtained.

COMPARATIVE EXAMPLE A

A reaction between VCHO and $M^H M^H$ was carried out as described in Example 5 except that 0.01 grams of the Karstedt platinum catalyst was substituted for the rhodium complex catalyst. The initial exotherm raised the reaction temperature to 125° C., at which point $M^H M^H$ addition was stopped. As the reaction mixture cooled, the mixture quickly became a hard, intractable gel.

EXAMPLE 6

153 grams of a devolatilized linear dimethylsiloxyhydrogen-stopped polydimethyl-methylhydrogen siloxane fluid, having a viscosity of 86 centistokes and containing 0.12% active hydrogen were weighted into a 500 cc flask with sufficient $RhCl(Ph_3P)_3$ added as a 2% solution in VCHO to provide approximately 5 ppm of Rh in the silicone fluid. This mixture was brought to 100° C. at which point 23.5 grams of VCHO were added dropwise. A brief exotherm to 108° C. accompanied the VCHO addition. The mixture was then maintained at 95° C. for 2 hours, at which point no SiH was detected via FTIR analysis. The batch was treated with approximately 50 ppm of $(CH_3)_3SiO[CH_3Si(OCH_2CH_2N(CH_3)_2)O]_{20}Si(CH_3)_3$ to stabilize the batch against acid-catalyzed thermally initiated ring opening polymerization. The batch was then stripped at 150° C. for an hour under pump vacuum to yield a epoxysilicone fluid having a viscosity of 335 centistokes of the formula $M^E D_{70} D_5^E M^E$.

COMPARATIVE EXAMPLE B

The reaction described in Example 6 was repeated except that the Karstedt platinum catalyst was substituted for $RhCl(Ph_3P)_3$. Although the batch did not gel during the VCHO addition, the final product after devolatilization was a fluid having a viscosity of 600 centistokes. The high viscosity of this epoxysilicone relative to that of the epoxysilicone produced in Example 6 is evidence that some degree of platinum-catalyzed polymerization occurred during the hydrosilation reaction in Comparative Example B.

EXAMPLE 7

370 grams of a $M^H D_{90} D_{20}^H M^H$ silicone hydride fluid having a viscosity of 123 centistokes and containing 0.27 weight % active hydrogen were weighed into a 2 liter flask with 370 grams toluene plus 4.3 grams of a 2% solution of $RhCl(Ph_3)_3$ in VCHO. The reaction mixture was heated to 97° C. with agitation at which point 128 grams of VCHO were added in 30 minutes. The batch temperature remained at 97°14 99° C. with no large exotherm. The mixture was maintained at 115° C. for 2 hours, after which no SiH was detected. 0.05 gram of $CH_3N(C_{18}H_{37})_2$ stabilizer was then added to the batch and the batch was then vacuum-stripped to 150° C. to remove solvent and other low boilers. The final product was an epoxysilicone fluid having a viscosity of 2486 centistokes at 25° C., a $N_{25}^D$ of 1.4368, and an epoxy equivalent weight of 500. Despite the extremely reactive nature of this polymer, no evidence of crosslinking was observed during its synthesis or workup.

COMPARATIVE EXAMPLE C

Two attempts to make the highly organofunctionalized polymer prepared in Example 7 using 5 ppm of the Karstedt catalyst as platinum, instead of $RhCl(Ph_3P)_3$ resulted in rapid viscosity build and gelation during the VCHO addition step.

EXAMPLE 8

The procedure described in Example 6 was repeated on a large scale in a 50 gallon stainless reactor. 250 pounds of the linear hydrogen-stopped polydimethyl-methylhydrogen siloxane fluid were charged to the kettle along with 25 pounds of toluene and 200 grams of a 2% solution of $RhCl(Ph_3P)_3$. The mixture was heated to 95° C. when 36.5 pounds of VCHO were fed into the reactor over a 45 minute period, with the reaction temperature maintaining at 90°-95° C. with no obvious exotherm. After a 2 hour hold at 100° C., all of the SiH had been consumed per FTIR analysis. 70 ppm of a toluene solution of methyl-2-dimethylaminoethoxy polysiloxane chain-stopped with trimethylsiloxy groups were added to stabilize the batch prior to devolatilization in a Thin Film Evaporator. Lab work-up of a small sample of this material (150° C. vacuum strip) afforded a 250 centistoke viscosity epoxysilicone fluid without any evidence of viscosity build or gel due to epoxy polymerization. The epoxy silicone prepared in this Example did not require dodecylmercaptan (used to poison platinum catalysts) and is processed with just one-half the amount of the stabilizer used in platinum-catalyzed systems. Thus, the rhodium catalyst simplifies processing and minimizes the potential for harmful gel formation during production.

EXAMPLE 9

226 grams of a devolatilized linear hydrogen-stopped polydimethyl-methylhydrogen siloxane fluid having a viscosity of 93 centistokes at 25° C. and 0.12% active hydrogen were weighed into a 1 liter flask, and sufficient $RhCl(Ph_3P)_3$ was added as a 2% solution in VCHO to provide approximately 5 ppm of rhodium in the reaction mixture. The mixture was heated with agitation to 102° C. 40 grams of VCHO were then added dropwise over a 20 minute period. The VCHO feed was accompanied by an exothermic response to 120° C. After all the olefin-epoxide was added, a 30 minute hold at 105° C. preceded FTIR analysis which confirmed that all available reactive SiH was consumed. 0.03 gram of $CH_3N(C_{18}H_{37})_2$ was then added to stabilize the produce, which was devolatilized under a vacuum pump and gentle nitrogen sweep at 155° C. for 100 minutes. The resulting fluid had a viscosity of 298 centistokes at 25° C. and a volatile content of less than 0.1%. No evidence of gel or crosslinking was detected. It should be noted that devolatilization under these conditions in the absence of this nonvolatile tertiary amine resulted in large amounts of gel formed in the product.

EXAMPLE 10

The procedure followed in Example 9 was repeated on a large scale, using the same 50 GL stainless reactor and the same inputs on the same scale used in Example 8 except that 100 ppm of $CH_3N(C_{18}H_{37})_2$ were substituted for 75 ppm of the siloxane stabilizer. This batch, like that in Example 8, was devolatilized in a Thin Film Evaporator unit. The product obtained in this Example was essentially identical to that produced in Example 8. The viscosities, solids content, and refractive indices for the products prepared in Examples 8 and 10 are provided in Table 1 below.

TABLE 1

| Example No. | Viscosity (centistokes) | Solids (per C-2) | Refractive Index |
|---|---|---|---|
| 8 | 204 | 99.0% | 1.4212 |
| 10 | 228 | 99.5% | 1.4204 |

EXAMPLE 11

100 grams of a low molecular weight fluid resin, approximate formula $M_2^H Q$, containing 0.9% wt % H (as SiH $Me_2 O_{17.8}$), were weighed into a 2 liter flask with 200 grams toluene and 1.0 grams of a 2% solution of $RhCl(Ph_3P)_3$ in VCHO. The agitating mixture was heated to 105° C., when 124 grams VCHO (1.0 mole) were added dropwise over a 3½ hour period. No exothermic response was observed. After a 1 hour hold at 110° C., a significant amount of unreacted SiH was detected via FTIR. Addition of 10 more grams VCHO followed by a 2 hour hold at 110° C. consumed all remaining SiH. 0.02 grams $MeN(C_{18}H_{37})_2$ were then added, and the batch was devolitalized at 100° C. using a Rototap. A viscous fluid product was obtained, 11000 cps viscosity, $N_D^{25} = 1.4806$.

Several attempts were made to carry out this synthesis using platinum hydrosilation catalysts. In each case, the reaction mixture rapidly built viscosity and formed a solid gel before all the VCHO was added to the reaction vessel, despite maintaining batch temperatures less than 60° C.

The reaction product of Example 11 made a clear solution when combined with 1 wt % (4-octyloxyphenyl) phenyliodonium hexafluoroantimonate. 2 mil coatings of this catalyst solution cured to a hard surface on a polyethylene Kraft substrate on exposure to 16 mJ/cm² focused ultraviolet light in an RPC QC1202 Lab UV Processor unit. This is an exceptionally fast uv cure response.

EXAMPLE 12

Example 12 illustrates that olefin epoxides other than VCHO can be reacted with SiH-containing compounds using a rhodium complex catalyst as the hydrosilation promoter.

228 grams of allylglycidylether (2.0 moles) were dispersed in 200 grams of toluene in a 1 liter round bottom flask. 0.02 grams of solid $RhCl(Ph_3)_3$ were added. This mixture was heated to 100° C. in order to dissolve the rhodium catalyst.

134 grams of sym-tetramethyldisiloxane (1.0 mole) were then slowly added to the reaction vessel over a 1 hour period. An induction period was observed; no exotherm occurred until about ½ of the disiloxane had been added, when a rapid temperature rise to 116° C. occurred (toluene reflux), which persisted throughout the addition. After a two hour hold at 110° C., a small amount of unreacted SiH was observed which was consumed by adding 20 more grams of allylglycidyl ether. Toluene and excess allylglycidyl ether were removed in vacuo to furnish 350 grams of a mobile fluid product, $N_D^{25}=1.450$ (literature value: 1.449).

The reaction product of Example 13 can be represented by the following formula

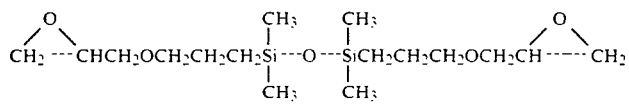

This synthesis confirms that olefin epoxides other than VCHO can be reacted with SiH-containing compounds using $RhCl(Ph_3)_3$, as the hydrosilation promoter. An identical reaction was run using the Lamoreaux-type platinum hydrosilation catalyst, i.e., $H_2PtCl_6$ in octanol, in place of $RhCl(Ph_3)_3$, but crosslinking occurred during the addition of $M^HM^H$ to allylglycidyl ether to the extent that the final product obtained was a viscous fluid, 180 cstk viscosity, compared to the 12 cstk fluid prepared in Example 12. The platinum-catalyzed reaction did not provide the desired product.

EXAMPLE 13

100 grams of $MD_4{}^HM$, containing approximately 1.0% H, were dispersed in 200 g toluene+0.75 of 2% $RhCl(Ph_3)_3$ solution in VCHO. This agitating mixture was brought to 100° C., when 130 g of VCHO (1.05 mole) were added over a 2 hour period. No exotherm occurred, and a strong SiH absorption remained in the FTIR spectrum of the reaction mixture. Incremental addition of 50 g excess VCHO+0.7 g more rhodium catalyst solution over a 9 hour period consumed all SiH present. The batch was treated with 0.02 g $CH_3N(C_{18}H_{37})_2$, then vacuum-stripped to 130° C. to remove toluene, excess VCHO and stray siloxane light ends. 215 grams of extremely viscous (more than 100,000 cps) fluid product were ultimately recovered, $N_D^{25}=1.4782$. This material can be represented as

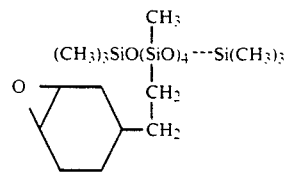

The extremely polar nature of this polymer causes its high viscosity; when heated to 60° C. the polymer readily flows, demonstrating that it did not crosslink to any significant extent during its synthesis. VCHO addition to $MD_4{}^HM$ could not be carried out in the presence of the Karstedt platinum catalyst. Gellation took place before half of the VCHO had been added to the hydride fluid.

EXAMPLE 14

Example 14 illustrates the usefulness of $RhCl_3.xH_2O$, rhodium (III) trichloride hydrate, as hydrosilation catalyst. Since $RhCl_3.xH_2O$ is normally the precursor from which other rhodium catalysts such as $RhCl(Ph_3)_3$ are derived, it would be less expensive to use than other rhodium catalysts because there would be no need for further processing of it prior to production of epoxysilicone fluids.

A 0.5 wt % solution of $RhCl_3.xH_2O$ in ethanol was prepared. 0.8 grams of this solution was weighed into a 1 liter reaction vessel with 240 grams of a non-devolatilized 16 cstk MeH-containing fluid approximately having the formula $MD_3{}^HD_{20}M$ and possessing 0.17% H, plus 40 grams of a 300 cstk dimethylvinyl-stopped dimethyl silicone fluid, having the approximate formula $M^{Vi}D_{100}M^{Vi}$. This mixture was 32 cstk prior to bringing it to 105°±5° C. for 2 hours, at which time the reaction mixture had 'pre-reacted' to the extent that its viscosity increased to 56 cstk. 50 grams of VCHO were then fed into this mixture over a 90 minute period at 105° C. without any obvious exotherm. Following a 2 hour hold at 110° C., FTIR analysis showed no reactive SiH remaining. 0.03 g of $CH_3N(C_{18}H_{37})_2$ stabilizer were added, and the batch was stripped of light ends, excess VCHO and so forth under pump vacuum at 150° C. for an hour, providing a hazy fluid product, 209 cstk, 99.0% solids, $N_D^{25}=1.4213$.

COMPARATIVE EXAMPLE D

The procedure followed in Example 14 was repeated using the same inputs, except that 0.03 grams of the Karstedt catalyst was substituted for the $RhCl_3.xH_2O$ solution. The 'pre-reaction' viscosity was 58 cstk, essentially the same as in Example 14, but the final devolatilized product was a 250 cstk fluid, 99.2% solids, $N_D^{25}=1.4220$. A significant viscosity increase resulted from platinum-catalyzed epoxy/SiH crosslinking.

EXAMPLE 15

A solution of $RhCl_3(n-bu_2S)_3$ in ethanol was prepared as described by Fergussen, et al., J. Chem. Soc 1965, 2627, which is hereby incorporated by reference herein. This solution was a clear, red liquid, 1.36% rhodium content.

VCHO addition to $M^HQ$ liquid resin was carried out as described in Example 11 except that 0.4 grams of the ethanolic $RhCl_3(n-bu_2S)_3$ solution was substituted for the $RhCl(Ph_3P)_3$ catalyst. The final product was a clear, viscous fluid having a viscosity of 12,000 centipoise at 25° C. and a $N_D^{25}$ value of 1.4812, excellent iodonium compatibility and UV cure response. As noted previously herein, this $M^EQ$ resin cannot be produced using the standard platinum hydrosilation catalyst.

The examples above illustrate that several different rhodium catalysts are useful for syntheses of epoxysilicone polymers and resins via regiospecific hydrosilation reaction of olefin-epoxides, most preferably VCHO, with SiH-containing substrates. The most significant consequence of this discovery is that highly organofunctional epoxysilicone polymers and resins, such as those described in Examples 11 and 15, may be readily and reproducibly prepared by simple addition of olefin epoxides to virtually any SiH-containing silicone precursor. Such syntheses are unpredictable and impractical when platinum catalysts are used.

What is claimed is:

1. A method for making an epoxyfunctional organosilicon compound, comprising the step or reacting at a temperature of from about 25° C. to about 100° C. a mixture comprising:
   (A) 1 part by weight of an ethylenically unsaturated epoxide;
   (B) from about 0.5 to about 400 parts by weight based on (A) of an organohydrogenpolysiloxane or organohydrogensilane; and
   (C) from about 1 to about 5000 parts per million based on (A) of a rhodium complex catalyst consisting of $RhX(R_3P)_3$ dissolved in 4-vinylcyclohexeneoxide wherein X is a halogen atom and R is an alkyl radical having from 1 to 8 inclusive carbon atoms, aryl, aralkyl, or alkaryl radical or the $R_3^1SiQ$- group in which Q represents a divalent aliphatic hydrocarbon radical having from 1 to 6 inclusive carbon atoms and $R^1$ represents an alkyl radical having from 1 to 8 inclusive carbon atoms, aryl, aralkyl, or alkaryl or a $(CH_3)_3Si$- radical.

2. A method according to claim 1 wherein component (A) is an ethylenically unsaturated epoxide selected from the group consisting of allyl glycidyl ether, methallyl glycidyl ether, 1-methyl-4-isopropenyl cyclohexeneoxide; 2,6-dimethyl-2,3-epoxy-7-octene; 1,4-dimethyl-4-vinylcyclohexeneoxide; 4-vinylcyclohexeneoxide; vinylnorborenemonoxide, and dicyclopentadienemonoxide.

3. A method according to claim 2 wherein component (A) is 4- vinylcyclohexeneoxide.

4. A method according to claim 1 wherein component (B) is a linear hydride polysiloxane or linear hydride silane.

5. A method according to claim 4 wherein component (B) is 1,1,3,3-tetramethyldisiloxane.

6. A method according to claim 1 wherein component (B) is a cyclic hydride polysiloxane or cyclic hydride silane.

7. A method according to claim 6 wherein component (B) is hydride cyclotetrasiloxane.

8. A method according to claim 1 wherein R is a phenyl group.

9. A method according to claim 1 wherein component (B) is present in an amount within the range of from about 0.5 to about 100 parts by weight.

10. A method according to claim 9 wherein component (B) is present in an amount within the range of from about 0.5 to about 100 parts by weight.

11. A method according to claim 9 wherein the rhodium catalyst is present in an amount within the range of from about 1 to about 500 parts per million based on component (A).

12. A method according to claim 9 wherein the rhodium catalyst is present in an amount within the range of from about 10 to about 50 parts per million based on (A).

13. A method for making an epoxyfunctional organosilicon compound, comprising the step of reacting at a temperature of from about 25° C. to about 100° C. a mixture comprising:
   (A) 1 part by weight of an ethylenically unsaturated epoxide;
   (B) from about 0.5 to about 400 parts by weight based on (A) of an organohydrogenpolysiloxane or organohydrogensilane; and
   (C) from about 1 to about 5000 parts per million based on (A) of a rhodium complex catalyst selected from the group consisting of $RhX_3(SR_2)_3$, and $RhX(CO)(R_3P)_3$; wherein X is a halogen atom and R is an alkyl radical having from 1 to 8 inclusive carbon atoms, aryl, aralkyl, or alkaryl radical or the $R_3^1SiQ$- group in which Q represents a divalent aliphatic hydrocarbon radical having from 1 to 6 inclusive carbon atoms and $R^1$ represents an alkyl radical having from 1 to 8 inclusive carbon atoms, aryl, aralkyl, or alkaryl or a $(CH_3)_3Si$- radical.

14. A method for making an epoxyfunctional organosilicon compound, comprising the step of reacting at a temperature of from about 25° C. to about 100° C. a mixture comprising:
   (A) 1 part by weight of an ethylenically unsaturated epoxide;
   (B) from about 0.5 to about 400 parts by weight based on (A) of an organohydrogenpolysiloxane or organohydrogensilane; and
   (C) from about 1 to about 5000 parts per million based on (A) of a rhodium complex catalyst consisting of $RhX_3(SR_2)_3$ wherein X is a halogen atom and R is an alkyl radical having from 1 to 8 inclusive carbon atoms, aryl, aralkyl, or alkaryl radical or the $R_3^1SiQ$- group in which Q represents a divalent aliphatic hydrocarbon radical having from 1 to 6 inclusive carbon atoms and $R^1$ represents an alkyl radical having from 1 to 8 inclusive carbon atoms, aryl, aralkyl, or alkaryl or a $(CH_3)_3Si$- radical.

* * * * *